United States Patent [19]

Lee

[11] Patent Number: 4,978,540

[45] Date of Patent: Dec. 18, 1990

[54] PRODUCTION OF FROZEN FOODS AND OTHER PRODUCTS

[76] Inventor: Tung-Ching Lee, 64 Higgins Dr., Kingston, R.I. 02881

[21] Appl. No.: 146,206

[22] Filed: Jan. 20, 1988

[51] Int. Cl.$^5$ ............................................. A23L 3/37
[52] U.S. Cl. ...................................... 426/61; 426/62; 435/2; 435/243; 435/832; 435/847; 435/876; 435/940; 435/886
[58] Field of Search ...................... 426/61, 62; 435/2; 424/101

[56] References Cited

U.S. PATENT DOCUMENTS 4,021,581  5/1977  Sing ...................................... 426/61

OTHER PUBLICATIONS

Maki, Applied Microbiology, Sep. 1974, p. 456.
Lindow Plant Disease, Mar. 1983, p. 327.
Lindow Phytopathology, vol. 76, p. 1069.
Lindow, Phytopathology, vol. 73, pp. 1097–1106.
Kozloff, J. Bacteriology, Jan. 83, pp. 222–231.
Phelps, J. Bacteriology, Aug. 86, pp. 496–502.
Corroto, EMBO Journal 5, pp. 231–236.
Derie, Phytopathology 76, p. 1117.
Paulin, vol. 2, INRA, pp. 725–731.
Anderson et al., Plant Physiol 80, 956–960.
Green et al., Nature 317, p. 645.
Kozloff et al., Science 226, 845–846.
Wobler et al., Proc. Nat. Acad. Sci., U.S.A. 83, 7256–7260.
Wobler et al., Biophysiol Journal 49 293a.
Makino Ann Phytopath Soc., Japan 48, pp. 452–457.
Duman et al., Ann Rev. Physiol 45, pp. 261–270.
Fall et al., J. Marine Research 43, pp. 257–265.
Arai et al., Agricultural and Biological Chemistry 50, pp. 169–175.

Primary Examiner—Sam Rosen

[57] ABSTRACT

The freezing of foodstuffs and other biological materials such blood products as sperm, ova, embryos and other tissues may be facilitated by applying thereto a non-toxic microorganism having an INA$^+$ phenotype or a biogenic ice nucleating agent or a functionally equivalent protein.

23 Claims, 2 Drawing Sheets

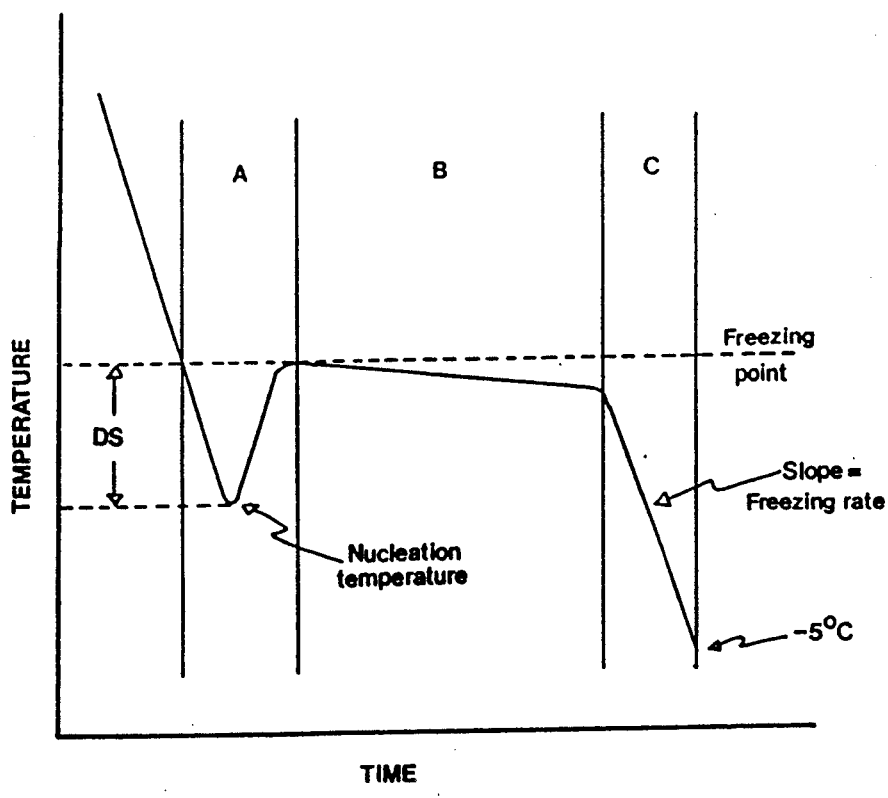
FIGURE 1 - Parameters measured using time-temperature data for freezing of fish muscle.
```
        A     - Nucleation Time
        B     - Plateau Time
        C     - Slope Time
    B + C     - Freeze Time
A + B + C     - Total Freeze Time
       DS     - Degree of Supercooling
```

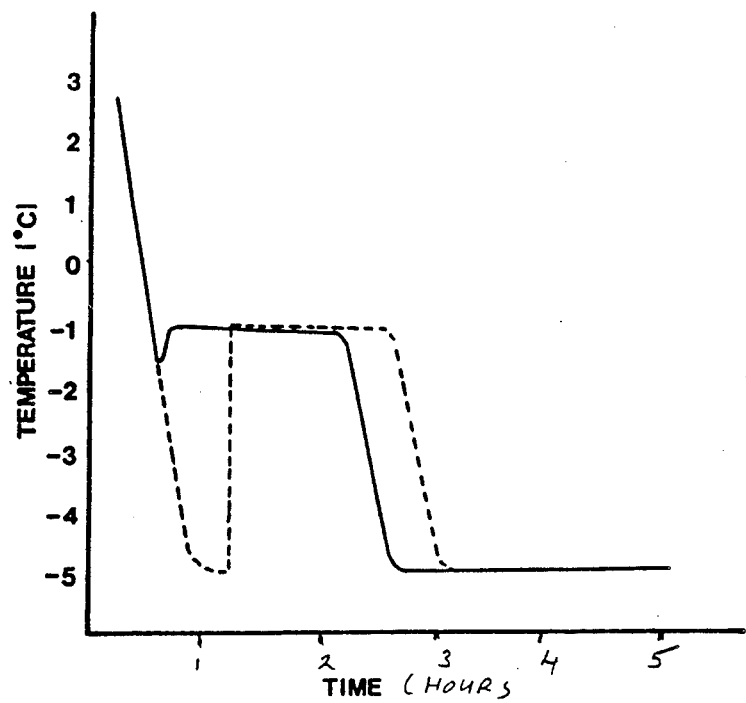
FIGURE 2 — Effect of addition of Pseudomonas syringae suspensions to whole salmon muscle when subjected to -5°C. Each curve represents equal sample sizes taken from separate fillets removed from 4 different fish.
Dashed line — Untreated fish muscle
Solid line — Treated fish muscle

PRODUCTION OF FROZEN FOODS AND OTHER PRODUCTS

BACKGROUND OF THE INVENTION

The present invention relates to the production of frozen products, particularly foodstuffs and other biological products.

Hiterto, in order to achieve satisfactory freezing of foodstuffs and other biological products, freezing operations have had to be operated at temperatures well below those at which such food products would theoretically be expected to freeze in order to avoid problems of super-cooling. Such super-cooling can occur in both intra-and extra-cellular moisture present in foodstuffs and other biological products and leads to a failure of the product to freeze satisfactorily. While the degree of super-cooling may vary substantially from batch to batch, the risk that super-cooling may occur has led food freezing practitioners to operate plants at temperatures as low as $-40°$ C. in order to avoid such risks. Furthermore, in such operations, foods or other biological products to be frozen are typically kept at such low temperatures for excessive periods of time to ensure that problems resulting from super-cooling are avoided. Not only does the requirement to use very low temperatures for prolonged periods result in very high energy costs, but also a further problem that arises from super-cooling is a tendency for ice crystals in the frozen foodstuff to grow to a large size thereby diminishing the organoleptic and textural properties of the frozen food. Similarly, the thaw drip loss (normally regarded as a measure of the quality of the frozen product) may increase if excessive super-cooling occurs during freezing. Conventional practice has been to try to avoid ice crystal growth resulting from super-cooling by effecting quick freezing of products. Alternatively, use has been made of additives such as emulsifiers in ice cream or cryoprotectants such as glycerol or sugar in other products. These techniques, however, require cooling to very low temperatures with the consequence that such techniques have high energy requirements.

The effects of certain ice-nucleating active agents produced by various bacteria on the nucleation of ice crystals have recently attracted interest, primarily because of their potential for producing artificial snow for ski slopes and because of their role in frost damage of growing plants. In particular, the ice nucleating properties of *Pseudomonas syringae* have been widely reported. (See, for example, Maki, et al Applied Microbiology, September 1974, p. 456). In recent years, these properties have been investigated with particular emphasis on the role played by *Pseudomonas syringae* of a protein derived therefrom in causing frost damage to growing plants (see for example Lindow, Plant Disease, March 1983, p. 327). Considerable press attention has been given to the allowability of experiments in the open environment involving mutants of *Pseudomonas syringae* that have been mutated to eliminate the gene that is responsible for the production of ice-nucleating protein. It is hoped by allowing these mutants to compete with *Pseudomonas syringae* that are naturally present on plants that the population of ice nucleating *Pseudomonas syringae* may be reduced (see, for example, Lindow, et al Phytopathology Vol. 76, No. 10, p. 1069 Abstract 95 (1986).

Similar ice nucleating properties have been reported for several other microorganisms including *Erwinia herbicola* (see, for example, Lindow, et al Phytopathology 73 1097–1106 (1983)) and Kozloff, et al J. Bacteriology Jan. 1983 p. 222–231), *Pseudomonas fluorescens* (see, for example, Phelps, et al J. Bacteriology Aug. 1986 p. 496–502)) and Corotto, et al (EMBO Journal 5 231–236 (1986)) and *Xanthomonas Camoestris* (Derie and Schaail, Phytopathology 76 (10) p. 1117 (1986), *Pseudomonas viridflava* (Paulin, et al Proc 4th Int. Conf on Plant Pathogenic Bacteria Vol. 2 INRA Beaucoaze France 1978 Vol. 2 p. 725–731 and Anderson and Ashworth, Plant Physiol Vol. 80 pages 956–960 (1986)).

A number of investigations of the specific genes or proteins produced by them that are responsible for ice nucleation have been reported. For example, Green and Warner in a letter to Nature 317 p. 645 (1985) describe the determination of the sequence of the ice nucleation gene from *Pseudomonas syringae* which they called inaZ. They noted that this contains several repeats of a sequence reiteration with the consensus repeat having the sequence GCCGGTTATGGCAGCACGCT-GACC, the gene having a total size of 4458. They also investigated whether deletion of fragments of inaZ affected the ability of the gene to produce an ice nucleating protein by inserting such modified genes into *E Coli*. It was found that in the case of deletions that did not result in a frameshift, ice nucleation properties were retained in a number of cases.

Corotti, et al in The EMBO Journal 5 p. 231–236 (1986) describe a DNA fragment of 75 kb obtained from *Pseudomonas fluorescens* that is capable of imparting ice L nucleating activity to *E Coli*. They designated their gene inaW. They also investigated the activity of inaW mutants and determined that insertions into a particular 3.9 kb sequence had particular effect on the activity of the gene. They concluded that the product of the gene, postulated to be a protein of about 180 kd molecular weight, was necessary to confer an ice nucleating (INA+) phenotype on *E coli*.

Kozloff, et al in J. Bacteriology 153 p. 222–231 (1983) hypothesize that the ice nucleating activity of *Pseudomonas syringae* and *E herbicola* stems from the presence of nucleating sites on their cell walls. Their results indicate that *Pseudomonas syringae* probably have 4–8 sites per cell and *E herbicola* 2 sites per cell.

Kozloff, et al in Science 226 845–846 (1984) suggest that a lipid phosphatidylinositol is present as well as a protein at ice nucleating sites or *Pseudomonas syringae* and *Erwinia herbicola*. Current thinking, however, now doubts this hypothesis.

Wobler, et al in Proc. Natl. Acad. Sci. USA 83 7256–7260 (1986) report the isolation of an ice nucleation protein from *E. coli* that have been transformed with a plasmid containing the inaZ gene obtained form *Pseudomonas syringae*. The protein (p 153) has an apparent molecular weight of 153 kd. The amino acid content of p153 corresponded closely with that predicted as the product of inaZ and the opening sequence of p153 (Met-Asn-Leu-Asp-Lys-Ala-Leu-Val-Leu-) corresponded exactly with the sequence that would be predicted to be coded by the inaZ gene. They further reported that a 180 protein obtained by a similar technique using the inaW gene obtained from *Pseudomonas fluorescens* apparently had similar sequences and structures to p153 obtained using inaZ. They suggest that the INA+ phenotype is conferred on both *Pseudomonas syringae* and *Pseudomonas fluorescens* by such proteins and that these proteins act as templates for ice nucleation even in the absence of the phospholipids Kozloff indicated to be necessary.

In Biophysical Journal 49 293a (1986) Wolber and Warner report that in the ice nucleating protein obtained from *Pseudomonas syringae*, the majority of the sequence consists of interlaced 8, 16 and 48 amino acid repeats. The secondary structure is apparently a β-sheet structure for repeated sequences punctuated by 5-6 turns per 48 amino acid unit. It is suggested that the protein folds into a regular structure built up from the 48 amino acid repeat and that this structure presents hydrogen bonding side chains that mimic the ice lattice.

Phelps, et al in J. Bacteriology 167 p. 496 (1986) indicate the proteinaceous nature of the ice nucleating material obtained from *Erwinia herbicola*, reporting that cell free ice nucleating agents could be obtained from outer membrane residues and that such agents could induce nucleation of water at temperatures in the range $-2$ to $-10°$ C. Makino in Ann Phytopath Soc. Japan 48 452-457 (1982) reports that ice nucleation activity was found in *Pseudomonas marginalis* but to a lesser extent than in *Pseudomonas syringae*.

In addition to studies on ice nucleating bacteria as noted above, studies have also been made of ice nucleation having a biogenic origin in other organisms. Thus, Duman and Horwath in Ann. Rev. Physiol. 45 261-70 (1983) review the role of ice nucleation proteins in the hemolymph of certain beetles in imparting freeze-tolerance to the beetles by inhibiting super-cooling and ensuring freezing of extra-cellular fluid at fairly high temperatures thereby reducing the risk of intracellular freezing. Such proteins are reported to exist in Vespula (which have 3-6 ice nucleation proteins) and Dendroides (having 1-2 ice nucleation proteins). The nature of the ice nucleating protein produced by *Vespula maculala* was investigated by Duman, et al in J. Comparative Physiology B 154 79-83 (1984).

Ice nucleating agents have also been reported as being produced by *Heterocapsia niei* (a marine dinoflagellate) by Fall and Schnell in J. Marine Research Vol. 43 pages 257-265 (1985).

Each of the above cited articles is incorporated herein by reference.

The use of bacteria having an INA+ phenotype (*Erwinia ananas*) to cause texturization of certain proteinaceous foods has been suggested by Arai and Watenabe in Agricultural and Biological Chemistry 50, 169-175 (1986). They added cells to aqueous dispersions or hydrogels of proteins and polysaccharides to convert bulk water into directional ice crystals at temperatures between $-5$ and $0°$ C. to form anisotropically textured products. Such products were produced using raw egg white, bovine blood, soybean curd, milk curd, aqueous dispersions or slurries of soybean protein isolate, hydrogel of agar, corn starch paste and hydrogels of glucomannan and calcium glucomannan. Such products are slowly cooled to $-5°$ C. in an air bath in the presence of the bacterial cells. The frozen products were then vacuum freeze dried at $-30°$ C. before setting by steaming to form flake-like textures. By slicing the products at right angles to the plane of the flakes, a textured product may be obtained.

When used herein the term ice nucleating phenotype (INA+) means an ability to induce nucleation of supercooled water at a temperature above $-20°$ C. For example, *P syringae* PV pisi has a nucleation temperature of $-2.9°$ C. according to Makino (Ann Phytopath Soc. Japan Vol. 48 pages 452-457 (1982)).

The term "non-toxic microorganism" when used herein means microorganism having no adverse effect on humans when ingested in the amounts that are likely to result from the use of such microorganism to assist in ice nucleation.

SUMMARY OF THE INVENTION

It is an object of the present invention to provide a means for freezing foodstuffs and other biological products that are frozen to preserve them, which reduces energy requirements for freezing by applying to said foodstuff or other biological product a non-toxic microorganism having an INA+ phenotype or an ice nucleating agent derived therefrom or a functionally equivalent agent so as to enable freezing to be effected without excessive super-cooling.

It is a further object of the invention to reduce the time taken to effect freezing typically of foodstuffs or other biological products.

It is now thought that in freezing foodstuffs and other biological products it is desirable to minimize the time that samples being frozen are held in the range 0 to $-5°$ C. since this is a temperature range in which many destructive enzymes are particularly active. It is an object of the present invention to increase the consistency of freeze times in freezing foodstuffs and other biological products so as to minimize the risk of prolonged exposure to these temperatures.

It is a further object of the present invention to provide a means for improving the quality of frozen food, such as fish or meat fillets by avoiding super-cooling to a degree that intra-cellular freezing occurs within muscle tissue of such foodstuffs.

A further advantage of the present invention is that it may improve the stability of the frozen product in cold storage where temperature fluctuations may cause deterioration of product quality, thereby improving the shelf life of such product and may allow for freezer to operate at a higher temperature.

Accordingly, from one aspect, the present invention provides a means for freezing solid foodstuffs and other biological products which comprises applying thereto a non-toxic microorganism having an INA+ phenotype or an ice nucleating agent derived from said microorganism or a functionally equivalent agent thereof and lowering the temperature of said solid foodstuff or other biological product to effect freezing thereof.

From a second aspect, the present invention provides a means for providing frozen foodstuffs or biological products which comprises applying thereto a non-toxic microorganisms having an INA+ phenotype or an ice nucleating agent derived from said microorganism or a functionally equivalent agent thereto and lowering the temperature of said foodstuff or biological product to effect freezing at atmospheric pressure and thereafter placing said foodstuff or biological product into cold storage without any further processing steps.

Without wishing to be bound by any theory, I believe that the ice nucleating agent produced by microorganisms having an INA+ phenotype is probably a protein.

BRIEF EXPLANATION OF THE DRAWINGS

FIG. 1 is a representation of an idealized freezing curve that is referred to for explanatory purposes.

FIG. 2 shows the freezing curves for untreated fish muscle and fish muscle treatment according to the present invention.

DETAILED DESCRIPTION OF THE INVENTION

Non-toxic microorganisms having a phenotype INA+ include natural bacteria having such properties, for example, *Erwinia ananas, Erwinia herbicola, Pseudomonas syringae* and *Pseudomonas fluorescens*. They also include other non-toxic bacteria that are naturally present in foodstuff, for example, species of Lactobacillus such as *Lactobacillus bulgaricus* and *lactobacillus acidophilus* and Streptococcus such as *Streptococcus lactus* and *Streptococcus thermophilus* that have been transformed by plasmids containing inaZ or inaW genes derived from *Pseudomonas syringae* or *Pseudomonas fluorescens* or the ice nucleating gene of one of the other microorganisms having an INA+ phenotype listed above or by an ice-nucleating sub unit thereof or a synthetic equivalent of such a gene or sub unit. Suitable means for producing such plasmids are described, for example, by Green and Warner (op cit) and Wobler (op cit). Introduction of such plasmids into suitable bacteria and cloning of such bacteria may be effected by standard methods of genetic engineering. It is also possible to introduce such genes into eukaryotic organisms such as yeasts. Many yeasts are present in foodstuffs and other biological products naturally. Such yeasts include various Saccharomyces such as *Saccharomyces cerevisiae, Saccharomyces carlsbergensis, Saccharomyces rosei, Saccharomyces rouxii,* and *Saccharomyces uvarum*. Introduction of genes to impart an INA+ phenotype to such yeasts may be accomplished by means of standard operations such as use of a plasmid shuttle vector containing the gene giving an INA+ phenotype or by use of an integrative DNA transformation involving removal of yeast cell wall, addition of a DNA fragment containing a gene coding for an INA+ phenotype in the presence of polyethylene glycol and then regenerating the cell wall.

Microorganisms having an INA+ phenotype may be employed live, as may often be the case with microorganism that are commonly present in food or dead. In the case when the microorganisms are killed prior to use, for example, by a heat treatment, care should be taken to avoid conditions that are so severe as to denature and deactivate the ice nucleating agent. For example, heating a suspension of the microorganism to a temperature at or near boiling may be appropriate.

Alternatively, ice nucleating protein itself may be used in the process of the present invention. Such proteins may be isolated from any of the microorganisms described above or indeed from other organisms that have been transformed to import an INA+ phenotype, such as *E. coli* as long as care is taken to isolate the desired protein prior to use. In such techniques, the gene coding for the INA+ phenotype is cloned and expressed in a suitable microorganism. The production of protein p153 in *E. Coli* is described in Wolber, et al Proc. Natl. Acad. Sci. US 83 7256-7260 (1986).

Recovery of the ice nucleating agents from the microorganism in which they have been produced may be accomplished by a variety of means. For example, in cases where the ice nucleating agent is expressed from the cell in substantial amounts recovery can be effected by centrifugation or filtration of the cell mass followed by dilation of the resulting pellet with a buffer (such as HEPES or phosphate) followed by refiltration and high speed centrifugation. In other cases, disruption of the cell may be required, for example, by ultra sonication, pressure shearing in a pressure bomb, solid shearing or enzymatic digestion using an enzyme such as a lysozyme. Following disruption of the cell, the cell mass may be centrifuged to remove undisrupted cells and the broken cell membrane containing the ice nucleating agent recovered. This material may then be centrifuged and washed with a neutral buffer prior to fractionation to recover the ice nucleating agent. Such fractionation may be carried out using standard techniques, testing each fraction obtained to determine the presence of the ice nucleating agent. In appropriate cases more than one fractionation, possibly using different techniques may be required. Suitable techniques include (a) Liquid-liquid extraction using organic solvents with varying polarity. This will remove less polar fractions and leave the proteins in the aqueous phase.

(b) Gel filtration chromatography—e.g. Sephadex G-200 and other molecular sieve packings will separate proteins based on their molecular size. Addition of sodium dodecyl sulphate (SDS) may be necessary to denature the tertiary and/or quaternary structure of proteins (if not already done). If SDS is used, dialysis of the resulting fractions will be necessary to remove the SDS.

(c) Ion exchange chromatography will separate the proteins based on their ionic charge. This technique can also be used for concentration, as dilute solutions of a protein can be loaded onto a column until the column is saturated, and then an eluting ion will strip the column of the protein.

(d) Hydroxylapatite chromatography—

(e) Preparative high pressure liquid chromatography using of the various types of column chromatography mentioned above with the addition of several others, e.g. reverse phase separations, under high pressure. This can result in greater speed and better resolution between fractions.

Foodstuffs that may be frozen by the process of the present invention include muscular foods such as fish and meat. For best results, however, the fish or meat should not be in pieces having excessive thickness. For example, the technique of the present invention is more suitable for use on fish fillets or steaks, or scallops of veal or beef steaks or poultry or pork or lamp chops than on a whole tuna fish or a side of beef. Satisfactory results have, however, been obtained when freezing certain types of fish whole (for example, trout and flat fish such as sole, flounder and plaice). Desirably, the flesh (whether it is fish or meat) should be pre-cut to a thickness no greater than 3 to 4 cm, preferably less than 1.5 cm in order to allow the ice nucleating microorganism or agent to penetrate the flesh. As an alternative to cutting the flesh into small pieces, it may be possible to obtain satisfactory results with large pieces into with deep cuts have been made. The process of the present invention is also useful for freezing comminuted meat or fish flesh such as sausages, ground beef and fish cakes. The techniques of the present invention may also find use in freezing of berries and other fruits and vegetables such as peas and corn that tend to suffer on freezing as a result of intra-cellular freezing. Again, however, best results are obtained on berries rather than, for example, on tomatoes, or other large fruits. The process of the invention may also be used for freezing other solid foods such as shell fish, food products such as pasta and bakery products such as cakes, bread and waffles. The invention may also be used to expedite the freezing of preprepared frozen meals such as so-called TV dinners and frozen snacks such as pizzas.

The process of the present invention may also be of use in the production of ice cream and other dairy products and similar products, for example, those based on tofu. Additional products that may be frozen in accordance with the present invention include fruit juice concentrates, frozen fruit bars such as popsicles, soy and other sauces, soups, yogurt and other such foods, for example fruit and vegetable purees. In such cases, in contrast to the process used by Arai and Watanabe described above, the ice nucleating microorganism or protein is mixed with the necessary ingredients and the whole is chilled en masse until it freezes. Such operations are typically carried out under normal atmospheric pressure and the products are not processed in any other way prior to storage.

In addition to such food products, the process of the present invention may also be of use in freezing other products that are typically frozen for storage such as blood products and other biological products such as sperm, ova embryos and other tissue. For example, the present invention may be used to freeze the sperm or ova of farm animals for breeding purposes.

In freezing food products according to the present invention, conventional freezer operations, such as blast or contact plate freezers or vacuum freeze driers may be used. However, typically they may be operated at temperatures 10° to 20° C. above those normally considered to be appropriate. Thus, satisfactory results may be obtained using the process of the present invention by operating a blast freezer at temperatures in the range $-5°$ to $-30°$ C. instead of $-20°$ to $-40°$ C. as is currently typical. Similarly contact plate freezing may be operated at temperatures in the $-15°$ to $-20°$ C. range in contrast to the $-30°$ to $-40°$ C. range which is normally used at present. Operating according to the present invention may also enable satisfactory freezing to be obtained in a reduced period as compared to present methods. The time taken will, however, depend upon the thickness of the foods items being frozen and also the packing of these items in the freezer.

The amount of material to be added to assist in ice nucleation according to the present invention will depend upon the nature of the material used and in particular on the temperature at which it will induce ice nucleation in super cooled water.

Since the ice nucleating microorganism or agents effectively act as catalysts for the nucleation of ice, only relatively small quantities are required to be applied in the foodstuff or other biological product that is to be frozen.

As noted above, the number of nucleation sites on a bacterium varies according to species (*Pseudomonas syringae* having 4–8 sites per cell and *E. herbicola* 2 sites per cell). Simple experiments will, however, enable one skilled in the art to determine an appropriate amount of bacteria having an INA+ phenotype to be used in a particular case.

*P. syringae* suspensions exhibit ice nucleating activities in distilled deionized water at concentrations of about $10^7$ colony forming units (c.f.u.) per ml and above. A concentration of $10^7$ c.f.u./ml is roughly equivalent to 1 mg dry weight of cell/ml. When using *P. syringae* in the present invention, I have found it convenient to use suspensions of bacteria having an aerobic plate count (APC) of $10^5$ to $10^8$ c.f.u./ml. Concentrations of bacteria in a suspension may be determined by absorbance of the suspension of light at 520 mm wavelength or other turbidimetric methods.

I have found that for the following foods, using a bacterial suspension having an aerobic plate count of $10^7$ c.f.u/ml, the following rates of application are suitable:

| Food | Bacteria having INA ± phenotype | Amount |
| --- | --- | --- |
| Salmon | Pseudomonas syringae | 0.02–0.2 ml suspension/g fish flesh |
| Trout | Pseudomonas syringae | 0.02–0.2 ml suspension/g fish flesh |

If one uses an isolated ice nucleating agent lower amounts of material need to be added to obtain the same concentration of nucleation sites. Thus, application of such agents in amounts of at least 0.0005 mg/g of food or biological products, for example 0.0015 to 0.01 mg/g of food or other biological product activities will normally be effective, although higher or lower amounts, for example, up to 0.1 mg/g may sometimes be useful.

The ice nucleating microorganisms or agents are added to foodstuffs or other biological products in ice nucleating amounts. Typically, for meat, fish and vegetables bacteria will be applied at a rate of at least $10^5$ cfu/g, for example in the range $10^6$–$10^7$ and in the production of ice cream or frozen tofu confectionery at a rate of at least $10^5$ cfu/ml. If an ice nucleating protein such as p153 is used, this may be applied at a rate of from 0.001 to 0.01 mg/g or more.

Said microorganisms or ice nucleating agents may be applied to foodstuffs and other biological products in any conventional way for example, for example, by spraying with aqueous dispersions of the ice nucleating material or, in the case of products such as ice cream, fruit juices, purees and the like by mixing the ice nucleating microorganism or agent intimately with the foodstuff that is to be frozen.

The process of the present invention is illustrated by the following Examples:

GENERAL

Source of Ice Nucleating Active Bacteria—*Pseudomonas syringae* pv pisi was obtained from American Type Culture Collection (ATCC) (Cat. #11043, Rockville, Md.). This bacteria was chosen as it is reported to be the most potent of the ice nucleating bacteria. *P. syringae* were revived, check for purity and stored.

Maintenance of bacteria—Bacteria were maintained on NAG plates and brothed and replated on a weekly basis. Three to seven day old (unless otherwise stated) colonies from NAG plates were routinely used as a source of *P. syringae*.

Preparation and application of bacteria—The bacteria were suspended in distilled water and the turbidity of the suspension adjusted to an absorbance of 1.0. One milliliter aliquots of the bacterial suspensions were applied to the samples in the test situations by either adding to the surface of the fish (minced or whole) or by mixing into the fish (minced). All suspensions were made on the day of use.

Fish used—Fish used in this study were obtained from the Department of Fisheries, Aquaculture and Pathology University of Rhode Island ponds. Atlantic salmon (*Salmo salar*) or rainbow trout (*Salmo gairdneri*) were anesthetized using tricain methane sulphonate MS-222 fish anesthetic (Argent Chemical Laboratories Inc. Redmond, Wa., killed by bleeding the artery and then eviscerated and headed. They were stored at 2°–4° C. in sealable plastic bags until use. An alternative source of live rainbow trout was a local supermarket. These were killed by a blow to the head and then similarly stored.

Sample Preparation—Fish were filleted and skinned by hand. Fillets were then prepared for either minced fish or whole fish experiments. For minced fish experiments, each fillet was diced finely using a sharp knife. Then fish muscle was put into a plastic centrifuge tube, and the tube placed into an assembly that allowed reproducible placement of thermocouple probe for subsequent freezing curve determination. For whole fish experiments each fillet was cut, perpendicularly to the backbone, into 4 cm pieces. A piece was then placed in an aluminum dish, and the dish likewise placed into an assembly that allowed reproducible placement of thermocouple probes for monitoring of the freezing curve. Both assemblies accommodated 4 samples.

Freezing Curves—Freezing curves were obtained using a Linseis Model 7040 4 channel chart recorded. Either premade Type T copper-constantin thermocouple probes (Model TJ36-CPSS-116G-6, Omega Engineering, Conn.) or lab made Type T copper-constantin thermocouples, both continually referenced against an ice bath, were used for all temperature measurements. Thermocouple junctions were welded using Helium thermocouple welder. Millivolt readings taken from the chart were converted to temperature (degrees Celsius) by use of a Basic program written by the author. Thermocouple probes were placed into each of 4 samples (minced or whole fish) and the assembly placed in a custom made chest freezer (Scientemp Corp. Adrian, Mich.). This freezer allowed user selection of temperatures from 0° C. to −20° C. with a +0.4° C. fluctuation of the chosen temperature. The inner chamber was double insulated and equipped with a fan for circulation. The lid of the chamber had a 12" square triple plated window to allow direct viewing of the specimen. An interior light was provided for illumination. Samples were placed in the chamber set at −5° C., −10° C. or −20° C. and the freezing curves monitored at these temperatures.

Definitions—FIG. 1 shows an idealized freezing curve showing actual temperatures in a sample against time when placed in a freezer at −5° C. The following times and temperatures were recorded for each of the 4 channels from the freezing curve:

Freezing Point—Defined as the temperature at which freezing occurred.

Nucleation Temperature—Defined as the minimum temperature attained by the sample before freezing occurred.

Supercooling—Defined as the temperature difference between the freezing point and nucleation temperature of the sample.

Nucleation Times—Defined as the time elapsed from the instant the sample passed through its freezing point temperature after freezing had occurred to the time at which nucleation commenced.

Freezing Times—Defined as the time elapsed from the instant the sample passed through its freezing point temperature to the instant it reached −5° C.

EXAMPLE 1

Minced fish samples prepared as described above were divided into control groups and groups to which *Pseudomonas syringae* dispersion of a concentration of $10^7$ c.f.u./ml was applied. The treated groups were sprayed with about 0.1 ml of dispersion per gram of minced fish. Freezing curves for the treatment and control samples were determined as described above. The results obtained are set out in Table 1.

TABLE 1

FREEZING CURVES FOR TROUT AND SALMON
Freezing Curve for −5°C.
Fish Preparation = Minced
Application Method = Surface - 1 ml of water or suspension to tube of 10 g fish

| Sample | Type of Fish | Age of Fish (Days) | Nucl. Time (Mins) | Nucl. Temp. (°C.) | Frz. Temp (°C.) | Super Cooling (°C.) |
|---|---|---|---|---|---|---|
| Control | Salmon | 1 | 66.6 | −4.5 | −0.8 | −3.7 |
| Control | Salmon | 1 | 4.2 | −1.3 | −0.9 | −0.4 |
| Test | Salmon | 1 | 6.0 | −1.3 | −1.0 | −0.3 |
| Test | Salmon | 1 | 6.6 | −1.6 | −1.2 | −0.4 |
| Control | Salmon | 2 | 24.3 | −3.6 | −0.6 | −3.0 |
| Control | Salmon | 2 | 69.0 | −4.7 | −0.9 | −3.8 |
| Test | Salmon | 2 | 5.7 | −1.2 | −0.6 | −0.6 |
| Test | Salmon | 2 | 6.0 | −1.7 | −1.0 | −0.7 |
| Control | Salmon | 4 | DID NOT FREEZE | | | |
| Control | Salmon | 4 | DID NOT FREEZE | | | |
| Test | Salmon | 4 | 6.0 | −1.9 | −1.0 | −0.9 |
| Test | Salmon | 4 | 6.0 | −2.0 | −1.1 | −0.9 |
| Control | Trout | 0 | 13.2 | −3.2 | −1.0 | −2.2 |
| Control | Trout | 0 | 13.8 | −3.4 | −1.1 | −2.3 |
| Test | Trout | 0 | 7.8 | −1.5 | −1.0 | −0.5 |
| Test | Trout | 0 | 5.4 | −2.1 | −1.2 | −0.9 |
| Control | Trout | 1 | 11.1 | −2.8 | −0.8 | −2.0 |
| Control | Trout | 1 | 12.6 | −3.0 | −0.8 | −2.2 |
| Test | Trout | 1 | 6.0 | −1.6 | −0.9 | −0.7 |
| Test | Trout | 1 | 5.4 | −1.6 | −1.0 | −0.6 |
| Control | Trout | 2 | 9.0 | −2.8 | −0.9 | −1.9 |
| Control | Trout | 2 | 6.0 | −1.9 | −0.9 | −1.0 |
| Test | Trout | 2 | 6.6 | −1.6 | −0.9 | −0.7 |
| Test | Trout | 2 | 5.4 | −1.7 | −1.0 | −0.7 |

[1]Time from killing to freezing

EXAMPLE 2

The procedure of Example 1 was repeated using eight samples of minced salmon muscle, these being subjected to a freezing environment of −5° C. Freezing curves were followed throughout the freezing cycle for these samples. The results (together with standard deviation in parentheses) are set out in Table 2 (total freezing time is the time taken to go from −1° C.—the appropriate freezing point of salmon muscle—to −5° C., it therefore includes nucleation time)

TABLE 2

| Sample | Super Cooling °C. | Nucleation Time (min) | Total Freezing Time (min) |
|---|---|---|---|
| Control | −3.7 (0.9) | 144.7 (155.7) | 332.3 (159.6) |
| Test | −0.6 (0.3) | 6.1 (0.3) | 219.4 (9.9) |

Further results obtained in the same way are as follows:

Degree of supercooling and nucleation times for 8 samples thoroughly diced and mixed salmon four of which were treated with *P. Syringae* as in Example 1 and four of which were untreated. The samples were taken from the same fillet and subjected to a −5° C. environment (Run 1). Run 2 represents the same samples having been thawed and refrozen. The results are set out in Table 3.

TABLE 3

| Sample | Nucleation Time (min) RUN 1 | Nucleation Time (min) RUN 2 | Degree of Supercooling (°C.) RUN 1 | Degree of Supercooling (°C.) RUN 2 |
|---|---|---|---|---|
| 1 untreated | DNF | DNF* | 5.6 | 5.6 |
| 2 | 40 | 417 | 5.2 | 5.6 |
| 3 | 97 | 42 | 5.6 | 4.9 |
| 4 | 193 | DNF | 5.6 | 5.6 |
| 5 treated | 4.2 | 4.8 | 0.4 | 0.4 |
| 6 | 5.4 | 4.2 | 0.2 | 0.3 |
| 7 | 4.8 | 5.4 | 0.4 | 0.4 |
| 8 | 4.8 | 4.8 | 0.2 | 0.4 |

*Does not freeze

Table 4—Freezing parameters for whole salmon when subjected to a −7° C. environment were determined with an without *P. syringae.*

| Sample | Temp. of Freezer (°C.) | Super-cooling (°C.) | Nucl. Time (mins) | Plateau Time (mins) | Slope Time (mins) | Freeze Time (mins) | Total Time (mins) |
|---|---|---|---|---|---|---|---|
| Control | −7.0 | −3.9 | 68.9 | 74.4 | 41.9 | 116.3 | 185.2 |
| | (±0.1) | (±1.5) | (±80.1) | (±13.6) | (±7.4) | (±18.7) | (±67.5) |
| Test | −7.0 | −0.8 | 4.6 | 86.1 | 43.6 | 129.7 | 134.3 |
| | (±0.1) | (±0.4) | (±1.0) | (±10.2) | (±4.1) | (±13.0) | (±13.2) |

All data are averages (standard deviations in parentheses) of 8 values

EXAMPLE 3

The methods of Example 1 were repeated but using fish fillets prepared as described in the introduction to the Examples. In this case for the test samples, the dispersions were applied at a rate of 0.1 ml dispersion of concentration $10^7$ c.f.u./ml per gram of fish.

The results obtained were as set out in Table 6 and shown in FIG. 2 for salmon.

TABLE 5

(Freezing Curve for −5° C.)

| Sample | Type of Fish | Age of Fish (Days)[1] | Nucl. Time (Mins) | Nucl. Temp. (°C.) | Frz. Temp (°C.) | Super Cooling (°C.) |
|---|---|---|---|---|---|---|
| Control | Salmon | 3 | 143.1 | −7 | −1.2 | −5.8 |
| Control | Salmon | 3 | 11.4 | −3.9 | −1.2 | −2.7 |
| Control | Salmon | 3 | 7.8 | −3.6 | −1.2 | −2.4 |
| Control | Salmon | 3 | 7.5 | −3.9 | −1.3 | −2.6 |
| Same as above except added P. Syringae after thawing and then refroze | | | | | | |
| Test | Salmon | 3 | 6 | −1.5 | −1.3 | −0.2 |
| Test | Salmon | 3 | 5 | −1.9 | −1.3 | −0.6 |
| Control | Salmon | 3 | 11.5 | −3.8 | −1 | −2.8 |
| Control | Salmon | 3 | 11.5 | −4.3 | −1.3 | −3 |
| Test | Salmon | 6 | 3.6 | −1.6 | −1.2 | −0.4 |
| Test | Salmon | 6 | 4.2 | −1.9 | −1.3 | −0.6 |
| Control | Salmon | 6 | 15.3 | −4.6 | −1.2 | −3.4 |
| Control | Salmon | 6 | 180 | −6.9 | −1.3 | −5.6 |
| Same lot of muscle tissue as used above, but different sample taken for freezing | | | | | | |
| Test | Salmon | 6 | 4.5 | −2.4 | −1.3 | −1.1 |
| Test | Salmon | 6 | 6 | −2 | −1.3 | −0.7 |
| Control | Salmon | 6 | 15 | −4.7 | −1 | −3.7 |
| Control | Salmon | 6 | 171 | −6.8 | −1.3 | −5.5 |

[1]Time in days from kill to freezing

EXAMPLE 4

The ability of *P. syringae* to induce ice nucleation in the following liquid foodstuffs was tested by adding 1 ml of a dispersion of *P. syringae* having a content of $10^7$ c.f.u./ml to 20 ml of liquid foodstuff and comparing the nucleation and freezing temperatures to samples treated in the same way, but to which no bacteria had been added was tested and the result set out in Tables 6, 7 and 8.

TABLE 6

(FREEZER SET AT −6° C.)

| Sample | With Bacteria Added: Average Nucleation Temp. °C. | With Bacteria Added: Average Freezing Temp. °C. | Control: Average Nucleation Temp. °C. | Control: Average Freezing Temp. °C. |
|---|---|---|---|---|
| Whole Milk | −1.9 ± 0.44 | −0.53 ± 0.5 | −6.13 ± .12 | −.63 ± .15 |
| Low Fat Milk | −2.8 ± 0.36 | −0.5 | −5.07 ± .71 | −0.53 ± 0.25 |
| Whipping Cream | −0.88 ± 0.095 | −0.55 ± 0.1 | −5.45 ± 1.83 | −0.59 ± 0.11 |
| Non-Dairy Creamer | −2.85 ± 0.71 | −0.86 ± 0.09 | −6.35 ± 0.3 | −1.0 ± 0.22 |
| Ice cream | −5.9 ± 0.02 | −3.9 ± 0.1 | DID NOT FREEZE | DID NOT FREEZE |

TABLE 7

(FREEZER SET AT −10° C.)

| Sample | With Bacteria Added: Average Nucleation Temp. °C. | With Bacteria Added: Average Freezing Temp. °C. | Control: Average Nucleation Temp. °C. | Control: Average Freezing Temp. °C. |
|---|---|---|---|---|
| Whole Milk | −1.25 + 0.13 | −0.72 + 0.13 | −5.12 + 1.57 | −.68 + 0.13 |
| Skim Milk | −1.2 + 0.2 | −0.53 + 0.05 | −5.51 + 0.87 | −0.5 + 0.05 |

TABLE 8

| | (FREEZER SET OF −16° C.) | | | |
|---|---|---|---|---|
| | With Bacteria Added | | Control | |
| Sample | Average Nucleation Temp. °C. | Average Freezing Temp. °C. | Average Nucleation Temp. °C. | Average Freezing Temp. °C. |
| Grapefruit Juice concentrate-[1] | −9.4 | −7 | −12.2 | −6.9 |
| Orange Sherbet | −8.5 | −4.2 | −9.15 | −4.9 |
| Apple Juice concentrate[2] * | −12.8 | −9.9 | −16.3 | −9.9 |

[1] 37.4% sugar
[2] 41.9% sugar
*Substantially similar results were obtained when using a dispersion of P. Syringae that had been subjected to microwave heating in a domestic microwave oven for 3 minutes.

EXAMPLE 5

The ability of *P. Syringae* to induce ice nucleation in model solutions typically used in food preparation containing salt and starch was tested in the same manner as the liquid foodstuffs in Example 4. The results are set out in Table 9.

TABLE 9

| Sample | Freezer Set at °C. | With Bacteria Added: Average Nucleation Temp. °C. | With Bacteria Added: Average Freezing Temp. °C. | Control: Average Nucleation Temp. °C. | Control: Average Freezing Temp. °C. |
|---|---|---|---|---|---|
| deionized water | −7 | −4.9 | −0.3 | DID NOT FREEZE | |
| 10% sucrose | −7 | −1.8 | −0.6 | DID NOT FREEZE | |
| 25% sucrose | −7 | −4.7 | −2.1 | DID NOT FREEZE | |
| 35% sucrose | −7 | −6.0 | −3.6 | DID NOT FREEZE | |
| 2% NaCl | −6 | −2.53 | −1.15 | −5.1 | 1.27 |
| 4% sucrose plus 4% sorbitol | −6.3 | −2.3 | −1.4 | | |

I claim:

1. A process for freezing solid foodstuffs separated from a growing environment which comprises applying to the surface or cuts in said solid foodstuff a non-toxic microorganism having an INA+ phenotype or a biogenic ice nucleating agent or a functionally equivalent protein capable of inducing ice nucleation and lowering the temperature of said solid foodstuff to effect freezing thereof.

2. A process according to claim 1 wherein said foodstuff is cooled into the range −5° to −30° C.

3. A process according to claim 1 wherein said non-toxic microorganism is selected from the group consisting of *Erwinia ananas, Erwinia herbicola, Pseudomonas syringae* and *Pseudomonas fluorescens.*

4. A process according to claim 1 wherein said non-toxic microorganism is a mutant bacterium that has been transformed by a plasmid importing an INA+ phenotype, said bacterium being selected from the group consisting of *Lacto bacillus bulgaricus, Lactobacillus acidophilus, Streptococcus lactis* and *Streptococcus thermophilus.*

5. A process according to claim 1 wherein said non-toxic microorganism is a mutant yeast that has been transformed to import an INA+ phenotype, said yeast being selected from the group consisting of *Saccharomyces cerevisiae, Saccharomyces rosei, Saccharomyces rouxii, Saccharomyces carlsbergensis* and *Saccharomyces uvarum.*

6. A process according to claim 1 wherein there is employed an ice nucleating protein selected from the group consisting of protein p153 protein p180 as and functionally equivalent sub units thereof capable of inducing ice nucleation.

7. A process according to claim 1 wherein a microorganism having a INA+ phenotype is added to meat in an amount of at least $10^6$ c.f.u./ml.

8. A process according to claim 1 wherein a microorganism having an INA+ phenotype is added to fish in an amount of at least $10^6$ c.f.u./ml.

9. A process according to claim 1 wherein a microorganism having an INA+ phenotype is added to vegetables in an amount of at least $10^6$ c.f.u./ml.

10. A process according to claim 1 wherein a biogenic ice nucleating agent or functionally equivalent protein is added to meat in an amount at least 0.001 mg/g.

11. A process according to claim 1 wherein a biogenic ice nucleating agent or functionally equivalent protein capable of inducing ice nucleation is added to fish in an amount of at least 0.001 mg/g.

12. A process according to claim 1 wherein a biogenic ice nucleating agent or functionally equivalent protein capable of inducing ice nucleation is added to vegetables in an amount of at least 0.001 mg/g.

13. A process according to claim 1 wherein a microorganism having an INA+ phenotype is added to a preprepared food product.

14. A process according to claim 1 wherein a microorganism having an INA+ phenotype is added to a pasta product.

15. A process according to claim 1 wherein a biogenic ice nucleating agent or functionally equivalent protein capable of inducing ice nucleation is added to a pasta product.

16. A process according to claim 1 wherein a microorganism having an INA+ phenotype is added to bakery products.

17. A process according to claim 1 wherein a biogenic ice nucleating agent or functionally equivalent protein capable of inducing ice nucleation is added to bakery products.

18. A process according to claim 1 wherein a microorganism having an INA+ phenotype is added to shell fish.

19. A process according to claim 1 wherein a biogenic ice nucleating agent or functionally equivalent protein capable of inducing ice nucleation is added to shell fish.

20. A process according to claim 1 wherein a biogenic ice nucleating agent or functionally equivalent protein capable of inducing ice nucleation is added to a prepared food product.

21. A process according to claim 1 wherein said freezing is carried out in a blast freezer.

22. A process according to claim 1 wherein said freezing is carried out in a contact plate freezer.

23. A process according to claim 1 wherein said freezing is carried out in a vacuum freezer drier.

* * * * *